United States Patent [19]

Pataschnick et al.

[11] Patent Number: 5,110,747
[45] Date of Patent: May 5, 1992

[54] DIESEL PARTICULATE MONITOR

[75] Inventors: Harvey Pataschnick; Georg Rupprecht, both of Voorheesville, N.Y.

[73] Assignee: Rupprecht & Pataschnick Company, Inc., Albany, N.Y.

[21] Appl. No.: 612,562

[22] Filed: Nov. 13, 1990

[51] Int. Cl.$^5$ .............. G01N 15/00; G01N 21/76; G01N 33/22
[52] U.S. Cl. .................. 436/133; 436/139; 436/144; 436/160; 436/177; 422/83; 73/23.31; 73/28.01; 73/28.04; 73/28.05; 110/217
[58] Field of Search ........... 436/133, 139, 145, 155, 436/157, 160, 171, 177; 422/93, 83; 73/23.31, 28.01, 28.04, 28.05; 110/217

[56] References Cited

U.S. PATENT DOCUMENTS

| | | | |
|---|---|---|---|
| 4,307,061 | 12/1981 | Sarholz | 422/94 |
| 4,391,338 | 4/1983 | Patashnick et al. | |
| 4,550,591 | 11/1985 | Cox et al. | 73/28 |
| 4,607,228 | 8/1986 | Reif | 324/454 |
| 4,775,516 | 10/1988 | Kempster et al. | 422/80 |
| 4,786,472 | 11/1988 | McConnell et al. | 422/61 |

FOREIGN PATENT DOCUMENTS

| | | | |
|---|---|---|---|
| 3009861 | 1/1988 | Japan | 436/133 |
| 858890 | 8/1981 | U.S.S.R. | |

OTHER PUBLICATIONS

Ohta, S. et al., "Measurement of Particulate Carbon in Urban and Marine Air in Japanese Areas", ATMOS Environment, vol. 18, No. 11 1984.
Osada, H. et al, "Real-Time Measurement of Diesel Particulate Emissions by the PAS Method using a $CO_2$ Laser", SAE Int. Congr. (Detroit Feb. 22-26, 1982 SAE Spec. Publ. N:P-107 245-251 (Feb. 1982).
Frey, J. W. et al., "Physical and Chemical Characteristics of Particles in a Diesel Exhaust", J. of Am. Ind. Hyg. Assoc. 28(5) pp. 468-478, Sep.-Oct. 1968.
Lach, G. et al., "Specific Problems of Sampling and Measuring Diesel Exhaust Emissions", SAE Passenger Car Meet. (Dearborn, Mich. Oct. 31-Nov. 11, 1988.
"Automated Carbon Analyzer for Particulate Samples", Steven H. Cadle, Analytical Chemistry, 1980, vol. 52, pp. 2201-2206.

Primary Examiner—James C. Housel
Assistant Examiner—David Redding
Attorney, Agent, or Firm—Heslin & Rothenberg

[57] ABSTRACT

Particulate concentration of diesel exhaust is measured by collecting the diesel particulate on a filter while measuring the amount of exhaust passing through the filter. The filtered particlate is then heated in an oxygen rich enviroment to oxidize carbon within the particulate to carbon dioxide. The amount of resulting carbon dioxide is measured to derive a corresponding measurement of the amount of filterd particulate. Particulate concentration is calculated by comparing the amount of particulate with the measured amount of exhaust passed through the filter. Filtered particulate can be heated incrementally to obtain a measurement of volatile components within the particulate prior to the oxidation of the non-volatile carbon component. The filter employed to collect the particulate is of a high temperature resistant type making it reusable and can be either integral with or inserted into the oxidation chamber of the instrument. Oxidation of the particulate inherently concurrently cleans the filter for reuse. Particulate can also be collected for analysis by using an accelerating impaction nozzle in conjunction with a heatable impaction plate.

32 Claims, 4 Drawing Sheets

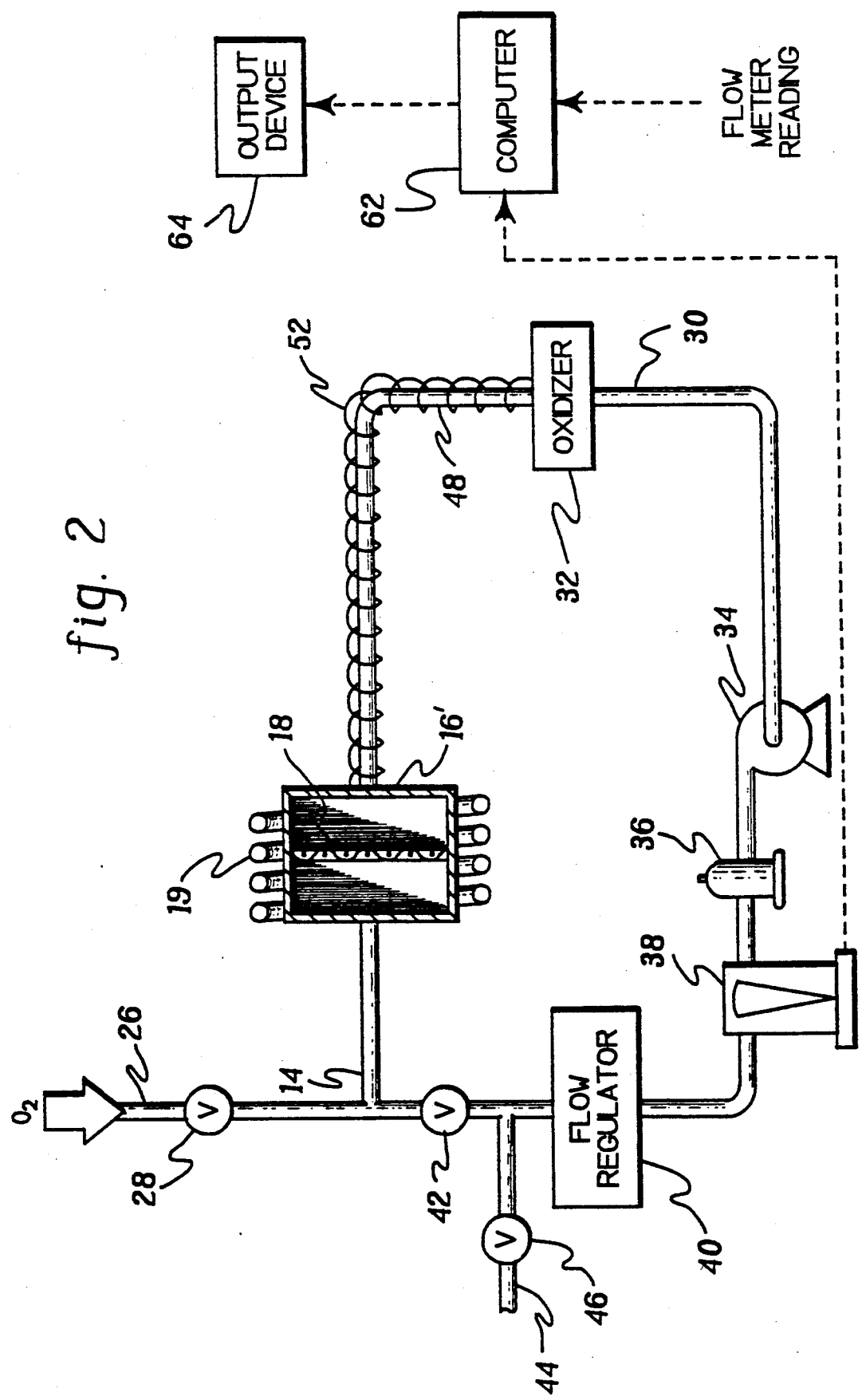

DIESEL PARTICULATE MONITOR

BACKGROUND OF THE INVENTION

The present invention relates generally to diesel engines, and more particularly to a technique for determining the particulate concentration of diesel exhaust.

The quality of air has become an important environmental concern within recent years. In an effort to curb air pollution and maintain air quality, strict vehicle exhaust emission guidelines have been set by federal and state authorities. Requirements for diesel emissions are extremely stringent because of the harmful effects of diesel exhausts within the atmosphere. Therefore, each diesel vehicle sold, for example within the United States, must pass certain emission tests and meet strict environmental emission standards. To determine if emission standards have been met, it is necessary to measure the particulate concentration of diesel exhaust. In order to accurately determine whether a diesel engine meets emission standards, a reliable reading of the particulate concentration of diesel exhaust is necessary. An inaccurate reading of diesel particulate concentration could result in a diesel engine improperly passing or failing emission tests. It is, therefore, desirable to utilize a technique for accurately and reliably measuring the particulate concentration of diesel exhaust.

Presently, diesel particulate is measured using a few different types of systems. One particular technique involves a direct measurement of the mass of particulate within exhaust on a real-time basis. With this technique a tapered element oscillating microbalance such as that shown in U.S. Pat. No. 4,391,338 is capable of measuring the mass of particulate deposited on a filter. This technique is not inexpensive and generally requires a dilution tunnel for proper use. Another technique for measuring the amount of particulate concentration of diesel exhaust involves optical measurements. This technique, however, suffers from a lack of accuracy and does not provide consistently reliable measurements of particulate mass. Another technique for measuring the particulate concentration of diesel exhaust involves forcing a measured amount of exhaust through a filter which collects the particulate therein, and then weighing the filter. The filter is preconditioned and preweighed so that the difference in weight of the filter before and after its use is representative of the amount of particulate within the exhaust. The disadvantage with this particular system is that it is extremely time consuming and labor intensive. Furthermore, the filter is not reusable after each measurement cycle thereby making it necessary to obtain a new filter for each diesel particulate measurement.

It is therefore an object of the present invention to provide a technique to accurately measure the particulate concentration of diesel exhaust.

It is also an object of the present invention to provide a technique for measuring the particulate concentration of diesel exhaust which is not labor intensive or time consuming.

It is also an object of the present invention to provide a technique for measuring the particulate concentration of diesel exhaust which utilizes a reusable filter to avoid the necessity of disposing of filters after they have been used to collect particulate.

It is also an object of the present invention to provide a technique for measuring the particulate concentration of diesel exhaust which provides consistently reliable readings.

It is also an object of the present invention to provide a technique to measure the concentration of non-volatile diesel particulate and/or volatile diesel particulate.

SUMMARY OF THE INVENTION

The shortcomings of the prior art are overcome and the objects of the present invention are achieved, by utilizing a technique for measuring particulate concentration of diesel exhaust in accordance with the present invention. The invention involves a method for determining the particulate concentration of diesel exhaust which includes filtering diesel exhaust to separate and collect particulate on a high efficiency filter, measuring the amount of exhaust filtered, exposing the filtered particulate to oxygen, heating the filtered particulate to oxidize carbon and form carbon dioxide, measuring the level of the resultant carbon dioxide to arrive at a level of carbon therein, and calculating the particulate concentration by comparing the level of carbon with the amount of exhaust measured.

The method may also include removing residual carbon dioxide gas from within the oxidizing environment prior to oxidation. The method may also include heating the filtered particulate incrementally to eliminate volatile components within the particulate prior to oxidation of the non-volatile carbon, and may further comprise calculating the volatile and/or non-volatile particulate components.

In a further aspect, the invention involves apparatus for determining the particulate concentration of diesel exhaust. The apparatus comprises a means for containing a filter for collecting diesel particulate from diesel exhaust, means for removing residual carbon dioxide from within the means for receiving the filter, means for supplying oxygen within the means for receiving the filter, means for heating the filter to oxidize carbon collected by the filter, and means for measuring the amount of carbon dioxide produced from the oxidation of carbon. The apparatus may also comprise a filter for collecting diesel particulate from diesel exhaust and a means for measuring the amount of diesel exhaust directed through the filter. The apparatus may further comprise a means for heating the filter incrementally to separate volatile from non-volatile components of the filtered particulate. The apparatus may also include means to oxidize such volatile particulate components to facilitate a separate measurement of the volatile components, and means for converting any CO produced by partial oxidation into $CO_2$.

A means for directing diesel exhaust through the filter may be included which comprises a diesel exhaust inlet mountable in fluid flow relationship between the filter and an exhaust pipe of the diesel engine. The means for supplying oxygen may comprise a valve means capable of directing air or other oxygen containing gas into the means for receiving the filter. The apparatus may further comprise valve means for preventing gas exiting the means for receiving a filter from entering the means for measuring the carbon dioxide or the means for measuring the amount of diesel exhaust directed through the filter, and a valve means for preventing diesel exhaust from flowing through the filter. The apparatus may further comprise a piping system interconnecting the means for receiving the filter, the means for oxidizing volatile particulate components, and the means for measuring the amount of carbon dioxide produced from the oxidation of carbon, in a closed loop. Pump means, pressure regulator means and/or flow regulator means may advantageously be incorporated in the closed loop. A section of the piping system connecting the means for containing the filter and the means for oxidizing volatile particulate components is preferably heated to prevent volatile components from condensing therein. The filter is preferably high temperature resistant to allow reuse and may be comprised of either a ceramic type trap or quartz fiber filter. The means for measuring the carbon dioxide may comprise an infrared absorption analyzer. The means for measuring the amount of filtered diesel exhaust may comprise a flowmeter, or a flow controller.

The filter may be built into the apparatus and the whole apparatus connected to an exhaust pipe or outlet of a diesel engine or vehicle under test. Alternatively, a separate sampling unit containing the filter and a means for measuring the amount of diesel gas passing through the filter can be connected to the exhaust pipe. After sampling, the particulate laden filter can be removed from the sampling unit and placed in a separate structure for oxidation of the particulate and measurement of resulting carbon dioxide.

In another aspect of the invention, the operation of the apparatus can be automated and a microcomputer or the like can be used to calculate the particulate concentration from the measurements of $CO_2$ and filtered diesel exhaust.

In a further aspect of the invention, the amount of different species of volatile particulate components may be determined by correlating $CO_2$ measurements with filter heating temperatures.

According to another aspect of the invention, rather than using a filter, diesel particulate can be collected by passing the diesel exhaust through an accelerating impaction nozzle and impacting exhaust particulate on a heatable impaction plate.

BRIEF DESCRIPTION OF THE DRAWINGS

These and other objects, features, aspects and advantages of the present invention will be readily understood from the following detailed description, when read in conjunction with the accompanying drawings, in which:

FIG. 2 illustrates another embodiment of the apparatus of the present invention for receiving a particulate laden filter and measuring particulate concentration of diesel exhaust.

In the drawings, like reference numbers are used to identify like parts.

DETAILED DESCRIPTION

Figure 1:
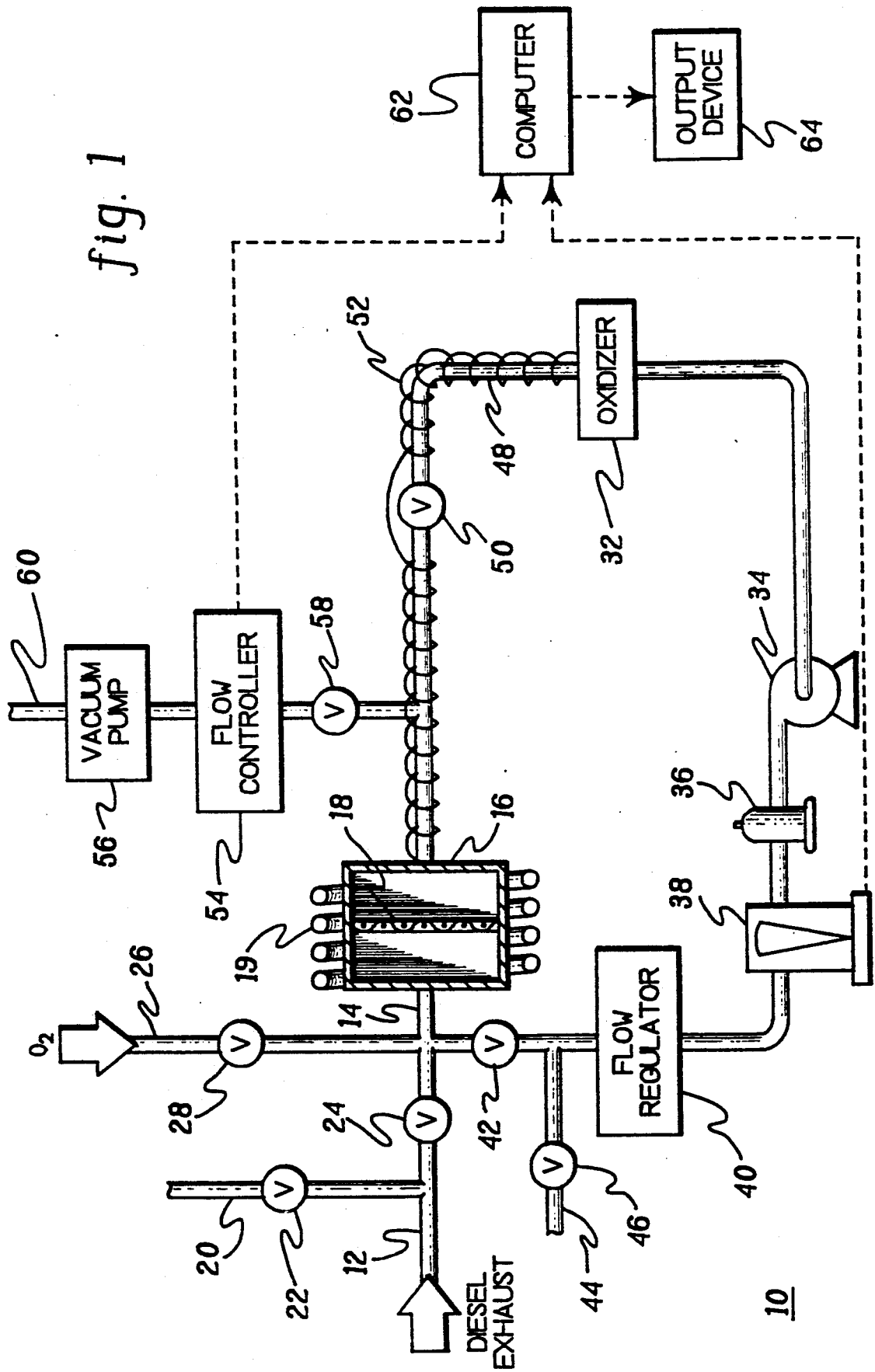
FIG. 1 depicts a first embodiment of the apparatus of the present invention employing a high efficiency filter and useful in sampling and in measuring the particulate concentration of diesel exhaust.

A first embodiment of apparatus for determining the particulate concentration of diesel exhaust, in accordance with the principles of the present invention, is shown in FIG. 1. The nature, function and interconnection of the components of the system will now be described, followed by a full description of the operation of the apparatus.

The apparatus 10 contains an inlet 12 which may be connected to the outlet end of an exhaust pipe of a diesel engine or diesel powered vehicle (not shown) thereby enabling the exhaust to flow through the inlet 12 and into the particulate concentration measuring system. The inlet 12 may be attached directly to the diesel exhaust pipe, or a flexible tubing or duct may be used to place inlet 12 in fluid flow relationship with the diesel exhaust pipe.

The inlet 12 is connected by a conduit passageway 14 to a chamber 16 capable of holding a filter 18 therein. A discharge nipple 20 with a valve 22 therein is located at a point between the inlet 12 and chamber 16. When the valve 22 is opened, diesel exhaust which flows through the inlet 12 will be allowed to flow through the discharge nipple 20 and out of the system. A valve 24 is located in the passageway 14 at a point downstream from the valve 22. When the valve 24 is opened, exhaust is allowed to flow towards the chamber 16. When the valve 24 is closed, however, exhaust is prevented from flowing towards the chamber 16 and any gas within the chamber 16 is prevented from flowing towards the valve 22 or inlet 12. A supply tube or nipple 26 is connected to the passageway 14 downstream from the valve 24 and upstream from the chamber 16. The supply nipple 26 has a valve 28 connected thereto and is connected to an oxygen rich purge gas supply. When the valve 28 is opened and the valve 24 is closed, oxygen rich purge gas is allowed to flow into and within the chamber 16.

The filter chamber 16 contains a filter 18 which is capable of filtering diesel particulate from diesel exhaust with high efficiency. Preferably, a high temperature resistant filter, such as a quartz fiber, or ceramic trap type, is employed, allowing for filter reuse. The filter 18 is mounted within the chamber 16 in such a fashion as to prevent exhaust gases from flowing through the chamber without flowing through the filter 18. A means for heating the chamber is contained within the system. The heating means may be in the form of a heating coil 19 surrounding the chamber 16 or alternatively may comprise a heating element or heating coil (not shown) within the chamber 16.

Chamber 16 is connected via a piping system 30 in fluid flow relationship and in a closed loop configuration with a series arrangement of oxidizer 32, pump 34, pressure regulator 36, carbon dioxide meter 38, flow regulator 40 and valve 42. During a measurement cycle, gases exiting chamber 16 are continuously circulated through this closed loop configuration.

Oxidizer 32 may comprise a simple heater such as a glowing nichrome wire, or heated platinum or nickel tubing, or may be a conventional catalytic converter available in the automotive industry. Oxidizer 32 can be advantageously employed to oxidize volatile particulate components, as well as to convert into carbon dioxide any carbon monoxide produced in chamber 16. These functions are more fully described hereinafter.

Pump 34 located downstream from oxidizer 32 serves to pump gases through the piping system 30. Pump 34 is preferably a unidirectional, internally sealed, closed circuit pump.

Gases output from pump 34 flow through pressure regulator 36 into $CO_2$ meter 38. Meter 38 can take many different forms but preferably is of an infrared absorption analyzer type. Such analyzers are commercially available in industrially hardened form. Pressure regulator 36 serves to reduce the pressure of gases entering meter 38 to a standard, e.g. ambient level, in order to maintain a constant pressure in $CO_2$ meter 38 and thereby avoid false indications due to pressure changes.

Flow regulator 40 is employed to maintain a constant flow through the closed loop configuration. Valve 42 serves to either permit or preclude fluid flow between regulator 40 and conduit 14 leading to chamber 16. An outlet pipe 44 is connected via valve 46 to piping system 30 between regulator 40 and valve 42.

The section 48 of piping system 30 connecting chamber 16 to oxidizer 32 includes a valve 50 and is surrounded by a heating coil 52 or other heating means. Valve 50 serves to control the flow of gases into oxidizer 32 while heater 52 is used to prevent volatile particulate components from condensing within pipe section 48.

A flow controller 54 and an associated vacuum pump 56 are connected via valve 58 to pipe section 48 at a point intermediate of chamber 16 and valve 50. Vacuum pump 56 serves to draw diesel exhaust through filter 18 in chamber 16 while flow controller 54 provides a measure of the amount of filtered diesel exhaust. Valve 58 provides a means for controlling flow through controller 54 and vacuum pump 56 to an outlet pipe 60. Instead of flow controller 54 and vacuum pump 56 a conventional flow meter can be used to measure the amount of diesel exhaust passing through filter 18. The pressure differential supplied by the diesel exhaust coming out of the engine may be used to drive the flow through chamber 16 and the flow meter.

An electrical signal representative of the amount of filtered diesel exhaust can be provided by flow controller 54 (or an equivalent flow meter) to a computer 62. Computer 62 also receives an electrical signal representative of the amount of carbon dioxide measured by meter 38. Computer 62 which can be a microprocessor or PC type computer determines, from these readings, the particulate concentration of the diesel exhaust. The particulate concentration can be displayed by an output device 64 connected to computer 62. Output device 64 may comprise, for example, a printer, meter or display device. Computer 62 can also be programmed in conventional fashion to control the operation of the valves, heating means and other components of the system in accordance with a desired schedule.

The system 10 operates to measure the particulate concentration of diesel exhaust by trapping diesel exhaust particulate within the filter 18 and measuring the volume of the exhaust which flows therethrough. After a sufficient amount of exhaust is filtered, oxygen rich gas is forced into the filter chamber 16 to drive out any exhaust fumes therein and provide an oxygen rich environment. The oxygen rich gas is also used to purge the closed loop measurement subsystem and to equalize the environment therein. The heating means is then activated to raise the temperature within the filter chamber to a sufficient level so that particulate trapped in filter 18, which particulate is nearly 100% carbon, oxidizes to carbon dioxide. Depending upon the temperature function used to heat the filter chamber, volatile particulate components may be driven off the filter without being oxidized. Oxidizer 32 serves to oxidize such volatile components as well as to convert any partially oxidized carbon in the form of carbon monoxide into carbon dioxide. The carbon dioxide is then measured by the carbon dioxide meter 38 to arrive at a carbon level. Since the particulate within the exhaust is nearly 100% carbon, a measurement of the amount of carbon within the exhaust yields the amount of particulate. The amount of exhaust measured to have flowed through the filter 18 is compared to the amount of particulate to arrive at a particulate concentration level. Oxidation of particulate trapped in the filter also serves to clean the filter sufficiently to allow it to be reused again in the same system. Therefore, there is no need to independently clean or to dispose of the filter after each sampling.

The system is used to measure the particulate concentration of diesel exhaust by attaching the inlet 12 to an exhaust pipe of a diesel powered vehicle so that the exhaust flows within the inlet 12. If the diesel engine is operating, the valve 22 should be opened and all other valves within the system closed so that the exhaust flows through valve 22 out of the system. To begin a sampling cycle, valve 24 and valve 58 are opened to allow exhaust to flow through the chamber 16 and filter 18, as well as through the flow controller 54, vacuum pump 56 and the outlet 60 of the system. Valve 22 may be closed completely, or partially if the filter is not capable of handling high exhaust capacity. As the exhaust flows through the filter 18, diesel particulate will be collected within the filter while the flow through the filter is measured using flow controller 54 or other suitable flowmeter.

After a predetermined period of time (or a predetermined volume or mass of exhaust flow through the system), the valve 24 can be closed and valve 22 opened to prevent exhaust from flowing through the filter and forcing exhaust to flow out the discharge nipple 20. Valve 28 is then opened to allow oxygen rich gas to flow into the chamber 16 and to force any residual carbon dioxide within chamber 16 out of the system through outlet pipe 60. After an appropriate period of time, valve 58 is closed and valves 50 and 46 are opened to purge the rest of the system (i.e. oxidizer 32, pump 34, pressure regulator 36, meter 38, flow regulator 40 and the interconnecting piping system 30) of any $CO_2$ left from the previous measurement cycle. The purged $CO_2$ leaves the system through outlet pipe 44. This last step also serves to equalize the environment in the filter chamber 16 and meter 38.

The oxygen rich gas connected to the supply nipple 26 and used to purge the system may be air or some other gaseous mixture containing a small percent of carbon dioxide in which case the purging process establishes a common background level of $CO_2$ in the closed loop of the system which can be measured by meter 38 and subtracted from subsequent reading to calculate the amount of diesel particulate. When measuring very minute amounts of diesel particulate it may be advantageous to use a $CO_2$-free gas for purging, such as pure oxygen or a mixture of oxygen and nitrogen. In this case, all $CO_2$ measured by meter 38 will be the result of oxidation of particulate.

After a sufficient period of time, any exhaust gas within the system will have been purged therefrom and the chamber 16 will be completely filled with oxygen rich gas. Valves 46 and 28 can then be closed and valve 42 opened to isolate the closed loop and prevent any gases circulating therein from escaping. The heater 19 can then be turned on to facilitate oxidation of the carbon within the filter 18.

In one mode of operation, the particulate on filter 18 can be rapidly subjected to a high temperature on the order of 700° C. to quickly burn off all of the particulate, both volatile hydrocarbon components and non-volatile carbon components. Oxidizer 32 ensures that all of the carbon in the particulate is converted into $CO_2$. The carbon dioxide meter 38 measures the resulting amount of carbon dioxide which is directly related to the amount of carbon oxidized. The amount of diesel particulate within the exhaust is substantially equal to the amount of carbon.

By comparing this amount of diesel particulate with the amount of exhaust measured by flow controller 54, particulate concentration can be determined. Computer 62, is connected to flow controller 54 and to carbon dioxide meter 38 and receives measurement readings therefrom. The output of meter 38 is a measurement of the parts per million of $CO_2$ in the recirculating gas stream within the closed measurement loop. Knowledge of the volume of the loop (gained through direct measurement or prior calibration by injection of known amounts of $CO_2$ into the loop) allows ready calculation of the number of molecules of $CO_2$ by the computer. Each molecule of $CO_2$ corresponds to an individual atom of carbon caught in the filter. From the number of carbon atoms, the mass of the carbon can be calculated in known fashion. The mass of the carbon is for all practical purposes equal to the mass of the particulate. Dividing the mass of the particulate by the measured amount of filtered diesel exhaust provides an accurate measure of particulate concentration. The computer can thus calculate the particulate concentration of the diesel exhaust from the measurement readings and provide an output signal representative of particulate concentration to an output device 64, e.g. a printer, meter or display device. Computer 62 can also advantageously be employed to control the operation of the valves, heating means and other components of the system in accordance with a desired schedule.

Since the diesel particulate is effectively 100% carbon, complete oxidation of the carbon within the filter cleans the filter entirely and allows it to be reused in the same system to again trap diesel particulate for oxidation into carbon dioxide. Accordingly, high efficiency filters which are also high temperature resistant can be effectively reused.

In an alternative embodiment of the system of the present invention, the exhaust particulate can be trapped within the high efficiency filter prior to the filter being placed into a chamber for oxidation. In such a system, exhaust does not have to flow into the system and the measurement apparatus need not be connected to a diesel exhaust pipe. The alternative embodiment, shown in FIG. 2, contains a conduit 26 connecting the chamber 16' to an oxygen rich gas supply and a valve 28 to allow the oxygen rich gas to flow into the chamber 16'. Chamber 16' is constructed to allow ready insertion of a particulate laden filter 18 therein.

The filter 18, is first placed within a separate sampling unit (not shown) for allowing exhaust to flow therethrough. In this embodiment, the sampling unit is connected to the exhaust pipe of a diesel engine vehicle and diesel particulate is trapped within the filter while the flow therethrough is being measured. After filtering a sufficient amount of particulate from the exhaust, the filter 18 can then be removed from the sampling unit and placed within the chamber 16'. The system is then used as previously described in the aforementioned embodiment. The valve 28 upstream of the chamber can be opened allowing the oxygen rich gas to enter chamber 16' therethrough and valve 46 can be opened while valve 42 remains closed in order to urge the measurement loop. Valves 46 and 28 are then closed and valve 42 opened to establish the closed loop recirculating gas stream. The means for heating the filter can then be activated to facilitate oxidation of the carbon in filter 18 into carbon dioxide. The carbon dioxide meter 38 determines the amount of carbon dioxide within the system. The output of $CO_2$ meter 38 and a flowmeter reading representative of the amount of filtered diesel exhaust are processed by computer 62 to determine the particulate concentration of the exhaust.

In a further aspect of the invention applicable to both of the previously described embodiments, volatile hydrocarbon components can be separated from the non-volatile carbon components of the particulate trapped in the filter. In this refinement, the filter with particulate trapped therein is heated incrementally (e.g. with a ramp function or in stages) in order to first drive off volatile components which can be oxidized into $CO_2$ by oxidizer 32 and measured by meter 38 and analyzed separately before the non-volatile carbon is oxidized.

Figure 4:
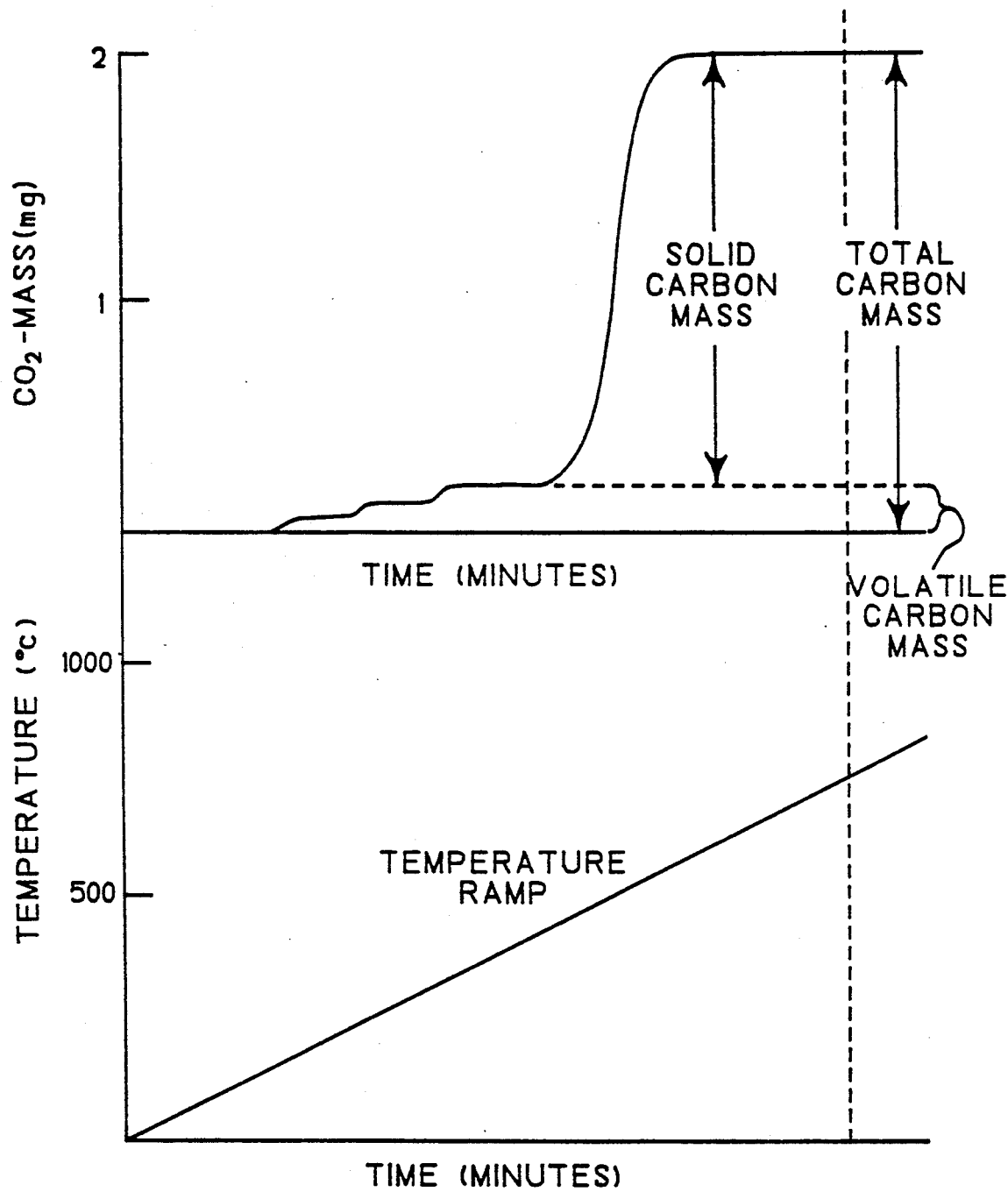
FIG. 4 presents an illustrative particulate heating temperature function and a corresponding $CO_2$ mass measurement profile useful in explaining how volatile and non-volatile particulate components can be measured.

As schematically illustrated in FIG. 4, the filter chamber can be heated along a temperature ramp at a particular rate; the rate depending in part upon the heat capacity of the filter chamber. As the heat gradually increases, volatile hydrocarbon components of the particulate evaporate off of the filter, without being oxidized in the filter chamber, and enter the circulating gas stream. Oxidizer 32 oxidizes the volatile components converting them to $CO_2$ which is measured by meter 38. As shown in the upper portion of FIG. 4, as the temperature in the filter chamber gradually increases other hydrocarbons are released from the filter, oxidized by oxidizer 32, and the resulting $CO_2$ measured by meter 38. Longer chain hydrocarbons have a lower vapor pressure and therefore evaporate later, i.e. at a higher temperature. Accordingly, as the temperature is gradually increased, there is a natural discrimination with respect to which species of hydrocarbons are released. The corresponding $CO_2$ measurements can therefore be used to provide insight into characterizing the amounts of various hydrocarbon constituents of the exhaust.

In the example illustrated, virtually all of the volatile particulate constituents have been driven off by the time the temperature reaches about 400° C. Heating beyond this temperature causes the non-volatile carbon to oxidize resulting in a substantial increase in measured $CO_2$. In the range of 700°-800° C., all of the carbon has been burnt off.

The section of piping between the filter chamber and oxidizer 32 is preferably heated to prevent any condensation of volatile hydrocarbons within this piping section.

Referring again to the $CO_2$ profile of FIG. 4, the top level provides a measure of the total carbon mass, both volatile and non-volatile, in the sample. The reading before the final plateau indicates the amount of volatile carbon components. The difference between the highest reading and the volatile carbon reading provides a measure of the mass of the non-volatile carbon. In this fashion, a measure of volatile to non-volatile components of the diesel particulate can be achieved.

Alternatively, two samples could be taken where one is totally oxidized and the other is heated first to drive off volatile components without oxidation and then the residue heated and oxidized. The latter sample yields a measurement of the non-volatile component which can be subtracted from the measurement of total sample to yield the amount of the volatile components.

Figure 3A:
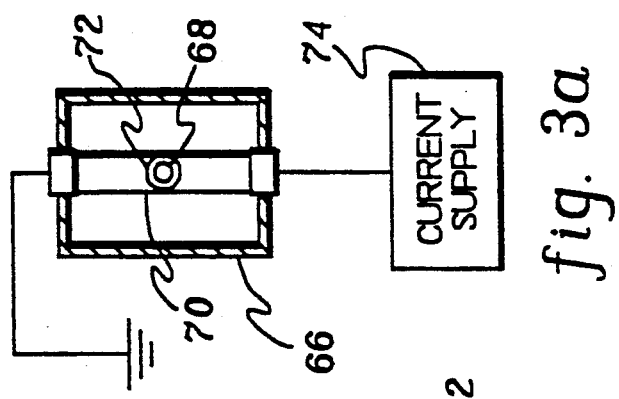
FIG. 3A illustrates further details of the impaction chamber equipment of FIG. 3.
Figure 3:
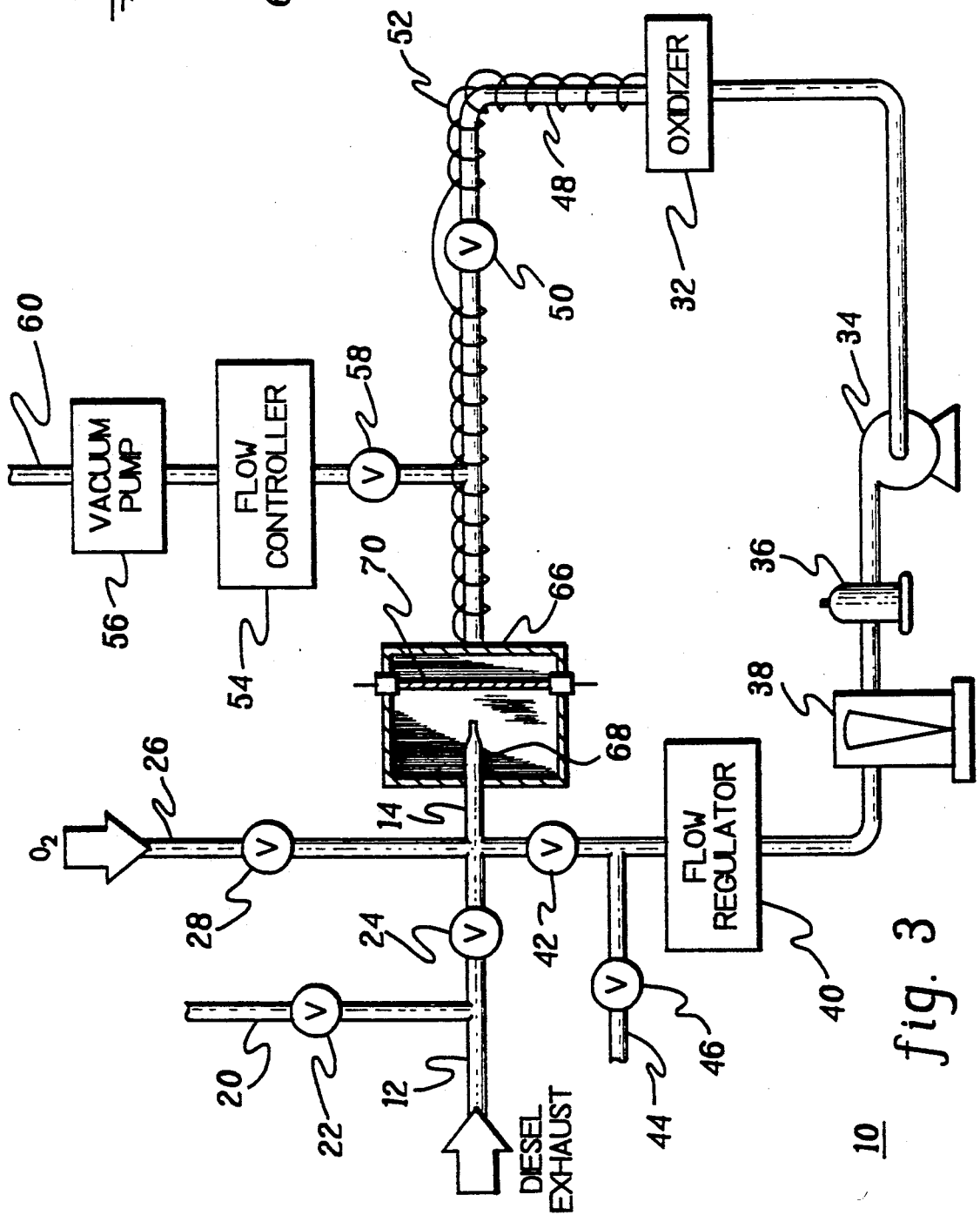
FIG. 3 illustrates an embodiment of the present invention employing an impaction nozzle and a heatable impaction plate within an impaction chamber used to collect diesel particulate.

FIGS. 3 and 3A depict an embodiment of the invention in which particulate is collected by impaction from a nozzle onto a heatable impaction plate, rather than with a filter. The system is identical to that previously described, except that the filter chamber and filter are replaced by an impaction chamber 66 containing an impaction nozzle 68 and a heatable impaction plate 70. In operation, the diesel exhaust is directed through acceleration nozzle 68 so that the particulate is impacted against and sticks to the heatable impaction plate 70. The particulate deposits in an impaction area 72 on the plate while the flow of exhaust gas continues around the plate and then out of the impaction chamber. Impaction plate 72 may comprise a small temperature controlled hot plate or a band of material through which a current can be run from a current supply 74 to cause the band to heat up. Once the particulate has been deposited on impaction plate 72, the measurement process is identical to that described earlier. One advantage of the impaction plate approach is that it allows the deposited particulate to be heated more directly than with a filter chamber. As in the filter examples, the deposited particulate is totally consumed upon oxidation allowing the impaction plate to be reused for future measurement cycles.

From the foregoing description, it will be apparent that a new method and apparatus for determining particulate concentration of diesel exhaust has been developed which can be advantageously employed to quickly and accurately determine whether a diesel powered vehicle is operating within emission standards. The measurement instrument can be made as both a research tool and also as a rugged, relatively inexpensive industrial grade device. It can produce particulate measurements in short periods of time with a minimum of labor requirements. Further, it does not require the use of a dilution tunnel and is immune to measurement confounding influences of water vapor in the exhaust. The process of the invention inherently renews the filter for future use, thereby avoiding the need to either independently clean or replace the filter after each measurement cycle. Another advantage is the ready susceptibility of the invention to automated/computer control. The present invention thus represents a significant advance in man's efforts to curb air pollution and maintain air quality.

Although the invention has been described with respect to the embodiments depicted herein, it is evident that the invention may be incorporated into a variety of different embodiments. All such embodiments are intended to be within the scope of the invention as defined by the following claims.

What is claimed is:

1. A method of determining particulate concentration of diesel exhaust comprising the steps of:
    filter diesel exhaust to separate and collect particulate on a high efficiency filter;
    measuring the amount of exhaust filtered;
    exposing the filtered particulate to oxygen;
    heating the filtered particulate to oxidize carbon within the particulate to carbon dioxide;
    circulating resultant carbon dioxide through a closed measurement loop;
    measuring the level of the resultant carbon dioxide within the closed measurement loop to arrive at a resultant level of carbon; and
    calculating the particulate concentration by comparing the level of carbon with the amount of exhaust measured.

2. The method of determining particulate concentration of diesel exhaust according to claim 1 further comprising the step of purging residual carbon dioxide gas from the vicinity of the filtered particulate with an oxygen rich gas prior to oxidation.

3. The method of determining particulate concentration of diesel exhaust according to claim 2 wherein the filtered particulate is heated incrementally to eliminate volatile components within the particulate prior to the oxidation of non-volatile carbon of said particulate.

4. The method of determining particulate concentration of diesel exhaust according to claim 3 wherein the volatile components of the particulate are oxidized into carbon dioxide and measured separately from the non-volatile carbon of said particulate.

5. The method of determining particulate concentration of diesel exhaust according to claim 1, further comprising the step of converting carbon monoxide which may be produced by partial oxidation of said carbon into carbon dioxide.

6. The method of claim 1, wherein the filtering step is performed with a filter which can withstand being heated to elevated temperatures necessary to fully oxidize the carbon within the particulate; and
    further comprising the step of reusing the filter to separate and collect particulate from diesel exhaust without further cleaning, conditioning or handling of the filter.

7. An apparatus for providing an indication of the level or concentration of particulate collected and retained by a filter from diesel exhaust, comprising:
    means for containing a filter having collected and retained diesel particulate;
    means for removing residual carbon dioxide from within the means for containing the filter;
    means for supplying oxygen within the means for containing the filter;
    means for heating a filter within said filter containing means to oxidize carbon of diesel particulate collected and retained by the filter;
    means for measuring the amount of carbon dioxide produced from oxidation of the carbon of said particulate; and
    means for establishing a closed recirculating gas measurement loop incorporating said means for containing a filter and said means for measuring the amount of carbon dioxide produced from oxidation of the carbon of said particulate; and means for providing an indication of the level or concentration of particulate based on the amount of carbon dioxide measured in said closed recirculating gas measurement loop.

8. The apparatus according to claim 7 further comprising means for (i) heating the filter incrementally to separate volatile components of the particulate and for (ii) oxidizing said separated volatile components of the particulate into $CO_2$ prior to oxidation of non-volatile carbon of the particulate.

9. The apparatus of claim 8, further comprising means for preventing unwanted condensation of said separated volatile components of the particulate.

10. The apparatus of claim 7, wherein the means for providing an indication comprises a computer means for calculating particulate concentration from the measured amount of carbon dioxide and a measurement of the amount of diesel exhaust passing through the filter during particulate collection.

11. The apparatus of claim 10 wherein said closed measurement loop further includes a separate oxidizer, a pump, a pressure regulator and a flow regulator.

12. An integral sampling and analyzing apparatus for providing an indication of the particulate concentration of diesel exhaust comprising:
a filter for collecting diesel particulate from diesel exhaust;
first means for containing the filter;
means for directing diesel exhaust into the first means and through the filter;
means for measuring the amount of diesel exhaust directed through the filter;
means for supplying oxygen in the first means to carbon within the diesel particulate collected by the filter;
means for heating the filter in the first means to facilitate the oxidation of the carbon within the particulate collected by the filter; and
means for measuring the amount of carbon dioxide obtained from the oxidation of the; and means for providing an indication of the concentration of particulate based on the measured amount of carbon dioxide obtained from the oxidation of the carbon within the particulate collected by the filter and the measured amount of diesel exhaust directed through the filter.

13. The apparatus for providing an indication of the particulate concentration of diesel exhaust according to claim 12 wherein the means for directing diesel exhaust through the filter comprises a diesel exhaust inlet mountable in fluid flow relationship between the filter and an exhaust pipe of a diesel engine or diesel powered vehicle.

14. The apparatus for providing an indication of particulate concentration of diesel exhaust according to claim 13 wherein the means for supplying oxygen comprises means capable of directing an oxygen containing gas from a supply of such gas to within the means for containing the filter.

15. The apparatus of claim 14 wherein the means for measuring the amount of diesel exhaust directed through the filter comprises one of a flowmeter and a flow controller.

16. The apparatus of claim 15 further comprising a piping system for connecting the means for containing the filter and the means for measuring the amount of carbon dioxide in a closed loop configuration.

17. The apparatus of claim 16 wherein the closed loop configuration further includes a separate oxidizer and a recirculating pump.

18. The apparatus of claim 16 further comprising means for selectively diverting diesel exhaust from flowing through the filter.

19. The apparatus of claim 12 wherein the filter has a high efficiency of particulate capture and a high temperature resistance.

20. The apparatus for providing an indication of the particulate concentration of diesel exhaust according to claim 19 wherein the filter is comprised of one of a ceramic filter and a quartz fiber filter.

21. A method of determining particulate concentration of diesel exhaust comprising the steps of:
collecting particulate from a measured amount of diesel exhaust;
exposing the collected particulate to oxygen;
heating the collected particulate to oxidize carbon within the particulate to carbon dioxide;
circulating resultant carbon dioxide through a closed measurement loop;
measuring the level of the resultant carbon dioxide within the closed measurement loop to arrive at a resultant level of carbon; and
calculating the particulate concentration by comparing the level of carbon with the measured amount of diesel exhaust.

22. The method of claim 21 wherein the collecting step comprises passing the exhaust through an acceleration nozzle and impacting the particulate upon a heatable impaction plate.

23. The method of claim 21 further comprising the step of purging residual carbon dioxide gas from the vicinity of the collected particulate with an oxygen rich gas prior to oxidation.

24. The method of claim 23 wherein the collected particulate is heated incrementally to evaporate volatile components of the particulate prior to oxidation of non-volatile carbon of said particulate; and further comprising the step of oxidizing the evaporated volatile components into carbon dioxide.

25. The method of claim 24 further comprising the step of converting carbon monoxide which may be produced by partial oxidation into carbon dioxide.

26. An integral collecting and measuring apparatus for providing an indication of the particulate concentration of diesel exhaust comprising:
collection means for collecting diesel particulate from diesel exhaust;
first means for containing the collection means;
means for directing diesel exhaust at the collection means in said first means;
means for measuring the amount of diesel exhaust directed at the collection means;
means for supplying oxygen in said first means to carbon within the diesel particulate collected by the collection means;
means for heating the collection means in said first means to facilitate the oxidation of the carbon within the particulate collected by the collection means; and
means for measuring the amount of carbon dioxide obtained from the oxidation of the; and means for providing an indication of the concentration of particulate based on the measured amount of carbon dioxide obtained from the oxidation of the carbon within the particulate collected by the collection means and the measured amount of diesel exhaust directed at the collection means.

27. The apparatus of claim 26 wherein said collection means comprises a heatable impaction plate; and said means for directing diesel exhaust at the collection means comprises an acceleration nozzle.

28. The apparatus of claim 26 wherein the means for directing diesel exhaust at the collection means comprises a diesel exhaust inlet mountable in fluid flow relationship between the collection means and an exhaust pipe of a diesel engine or diesel powered vehicle; and further comprising a pipe system connecting the first means and the means for measuring the amount of carbon dioxide in a closed loop configuration.

29. The apparatus of claim 26, wherein the means for providing an indication comprises a computer means for calculating particulate concentration from the measured amount of carbon dioxide and the measured amount of diesel exhaust.

30. An integral sampling and analyzing apparatus for providing an indication of the level of particulate in diesel exhaust comprising:

collection means for collecting diesel particulate from diesel exhaust;

first means for containing the collection means;

means for directing diesel exhaust at the collection means in said first means;

means for supplying oxygen in said first means to carbon within the diesel particulate collected by the collection means;

means for heating the collection means in said first means to facilitate the oxidation of the carbon within the particulate collected by the collection means; and means for measuring the amount of carbon dioxide obtained from the oxidation of the; and means for providing an indication of the concentration of particulate based on the measured amount of carbon dioxide obtained from the oxidation of the carbon within the particulate collected by the collection means.

31. The apparatus of claim 30 wherein the means for directing diesel exhaust at the collection means comprises a diesel exhaust inlet mountable in fluid flow relationship between the collection means and an exhaust pipe of a diesel engine or diesel powered vehicle; and further comprising a piping system connecting the first means and the means for measuring the amount of carbon dioxide in a closed loop configuration.

32. The apparatus of claim 31 further comprising:

means for measuring the amount of diesel exhaust directed at the collection means; and wherein means for providing an indication comprises a computer means for determining particulate concentration from the measured amount of carbon dioxide and the measured amount of diesel exhaust.

* * * * *

UNITED STATES PATENT AND TRADEMARK OFFICE
CERTIFICATE OF CORRECTION

PATENT NO. : 5,110,747
DATED : May 5, 1992
INVENTOR(S) : Harvey Patashnick, et al It is certified that error appears in the above-indentified patent and that said Letters Patent is hereby corrected as shown below:

On the title page, Item [19] "Pataschnick et al." should read
--Patashnick et al--
On the title page, Item [75] "Pataschnick" should read --Patashnick--
On the title page, Item [56] line 8, "filtered" should read --filtered--
Column 6, line 25 "sc" should read --so--
Column 9, line 66 "filter" should read --filtering--

Signed and Sealed this

Twenty-fifth Day of January, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,110,747
DATED : May 5, 1992
INVENTOR(S) : Harvey Patashnick and Georg Rupprecht It is certified that error appears in the above-indentified patent and that said Letters Patent is hereby corrected as shown below:

Col. 11, line 32: insert —carbon— before ";"
Col. 11, line 57: delete "for" before "connecting"
Col. 12, line 55: insert —carbon— before ";"
Col. 13, line 4 : substitute —piping— for "pipe"
Col. 14, line 4 : insert —carbon— before ";"

Signed and Sealed this

Ninth Day of April, 1996

Attest:

BRUCE LEHMAN

Attesting Officer    Commissioner of Patents and Trademarks